United States Patent
Paganelli et al.

(10) Patent No.: US 10,135,079 B2
(45) Date of Patent: Nov. 20, 2018

(54) FUEL CELL SYSTEM EQUIPPED WITH A HYDROGEN LEAKAGE DETECTOR

(71) Applicants: COMPAGNIE GENERALE DES ETABLISSEMENTS MICHELIN, Clermont-Ferrand (FR); Michelin Recherche et Technique S.A., Granges-Paccot (CH)

(72) Inventors: Gino Paganelli, Clermont-Ferrand (FR); Lionel Jeanrichard, Clermont-Ferrand (FR)

(73) Assignee: Compagnie Generale des Etablissements Michelin, Clermont-Ferrand (FR)

( * ) Notice: Subject to any disclaimer, the term of this patent is extended or adjusted under 35 U.S.C. 154(b) by 18 days.

(21) Appl. No.: 14/652,557

(22) PCT Filed: Dec. 18, 2013

(86) PCT No.: PCT/EP2013/077012
§ 371 (c)(1),
(2) Date: Jun. 16, 2015

(87) PCT Pub. No.: WO2014/095948
PCT Pub. Date: Jun. 26, 2014

(65) Prior Publication Data
US 2015/0325867 A1    Nov. 12, 2015

(30) Foreign Application Priority Data

Dec. 19, 2012    (FR) .................................... 12 62342

(51) Int. Cl.
*H01M 8/04* (2016.01)
*H01M 8/04089* (2016.01)
(Continued)

(52) U.S. Cl.
CPC ........ *H01M 8/04089* (2013.01); *G01N 27/14* (2013.01); *G01R 31/00* (2013.01);
(Continued)

(58) Field of Classification Search
CPC ........... H01M 8/04089; H01M 8/0444; H01M 8/04664; H01M 8/04686; G01N 27/14; G01R 31/00
See application file for complete search history.

(56) References Cited

U.S. PATENT DOCUMENTS

| | | | |
|---|---|---|---|
| 5,435,180 A | 7/1995 | Uchiyama et al. | 73/204.19 |
| 5,896,487 A | 4/1999 | Masten et al. | 388/811 |

(Continued)

FOREIGN PATENT DOCUMENTS

| CN | 1604378 A | 4/2005 |
|---|---|---|
| DE | 10 2011 103 248 A1 | 12/2012 |

(Continued)

OTHER PUBLICATIONS

International Search Report dated Feb. 7, 2014, issued by WIPO in connection with International Application No. PCT/EP2013/077012.

*Primary Examiner* — Gregg Cantelmo
(74) *Attorney, Agent, or Firm* — Fitzpatrick, Cella, Harper & Scinto

(57) ABSTRACT

A fuel cell system includes a stack of electrochemical cells, a sensor, and a microcontroller. Each cell of the stack includes an electrode plate having a face in electrical contact with an electrolyte. At least one tube is connected to the face of each cell in a circuit for exchanging a gas with an area exterior to the stack. The sensor is sensitive to a concentration of the gas in air surrounding the stack. A sensitive unit of the sensor is exposed directly to an in situ quantity of a component of the gas. The microcontroller generates and (Continued)

outputs an analog signal corresponding to concentration information, based on a concentration measurement, and generates and outputs an analog signal indicating an operation status of the sensor.

7 Claims, 2 Drawing Sheets

(51) Int. Cl.
    *G01N 27/14*     (2006.01)
    *G01R 31/00*     (2006.01)
    *H01M 8/0444*     (2016.01)
    *H01M 8/04664*     (2016.01)

(52) U.S. Cl.
    CPC ..... *H01M 8/0444* (2013.01); *H01M 8/04664* (2013.01); *H01M 8/04686* (2013.01)

(56) References Cited

U.S. PATENT DOCUMENTS

| | | | |
|---|---|---|---|
| 6,401,018 B1* | 6/2002 | Oba | B60K 6/46 180/65.245 |
| 2004/0005494 A1* | 1/2004 | Drake | C01B 3/32 429/410 |
| 2005/0074644 A1 | 4/2005 | Ueda et al. | 429/22 |
| 2005/0155405 A1* | 7/2005 | Sasaki | G01N 27/16 73/1.06 |
| 2006/0289400 A1 | 12/2006 | Takahashi | 219/121.36 |
| 2007/0024326 A1* | 2/2007 | Faust | G06F 1/025 327/105 |
| 2007/0028666 A1 | 2/2007 | Sasaki et al. | 73/23.21 |
| 2008/0026263 A1 | 1/2008 | Leboe et al. | 429/13 |
| 2009/0128160 A1 | 5/2009 | Chiaburu et al. | 324/537 |
| 2009/0151437 A1* | 6/2009 | Saunders | F01N 13/00 73/114.73 |
| 2009/0210171 A1 | 8/2009 | Fu | 702/35 |
| 2010/0209787 A1 | 8/2010 | Kajiwara et al. | 429/400 |
| 2010/0233562 A1 | 9/2010 | Kajiwara et al. | 429/444 |
| 2011/0302993 A1 | 12/2011 | Kuebel | 73/23.31 |
| 2012/0237843 A1 | 9/2012 | Paganelli | 429/429 |
| 2014/0227571 A1 | 8/2014 | Paganelli et al. | 429/90 |

FOREIGN PATENT DOCUMENTS

| | | |
|---|---|---|
| EP | 0 291 462 A2 | 11/1988 |
| EP | 0 501 089 A1 | 9/1992 |
| EP | 1 505 385 A1 | 2/2005 |
| EP | 1 521 325 A2 | 4/2005 |
| EP | 2 522 974 A2 | 11/2012 |
| FR | 2 412 055 A1 | 7/1979 |
| FR | 2 966 241 A1 | 4/2012 |
| JP | 57-149936 A | 9/1982 |
| JP | 03105600 A * | 5/1991 |
| JP | 2003-302362 A | 10/2003 |
| JP | 2010-019754 A | 1/2010 |

* cited by examiner

FUEL CELL SYSTEM EQUIPPED WITH A HYDROGEN LEAKAGE DETECTOR

FIELD OF THE INVENTION

The present invention concerns fuel cell systems. More particularly, it relates to devices making it possible to carry out measurements with a view to monitoring the state of this equipment and its operational management.

PRIOR ART

Fuel cells are currently the subject of numerous studies in the scope of efforts made to limit pollution of the environment, particularly in transport. Among those most studied currently are undoubtedly hydrogen fuel electrolytic generators, using air or pure oxygen as an oxidant. The use of solid electrolytes in the form of polymer membranes impregnated with water has allowed significant progress. On the other hand, there is also the development of electrolysers, particularly in order to store electrical energy in the form of chemical energy.

One of the main subjects to be addressed in the scope of developing these new solutions is that of safety. Specifically, fuel cells use gases taken from the atmosphere, but also gases stored under pressure. However, it has been found that undesirable diffusion of these gases can occur, either directly at the storage means or during transfer of this gas from the storage to the fuel cell. Since some of these gases are inflammable, it is necessary to be able to detect their leakage rapidly, in order to avoid accidents which are dangerous for the users of the cells. Furthermore, in order not to interfere with the operation of fuel cells superfluously, it is useful to be able to avoid any false leak detection, which would for example lead to unnecessary shutdown of the cell.

Thus, sensors for the concentration of a gas, in particular hydrogen, in gases of the environment of fuel cells have been developed in recent years. Such sensors are based on measuring thermal conductivity with the aid of a sensitive unit having a heating resistor, the heating or dissipative cooling of which depends on the thermal conductivity of the ambient gas and therefore in general on its composition. These sensors, which are relatively compact and simple to use, are particularly suitable for measurements of the level of hydrogen in a gas because of the very high thermal conductivity of hydrogen compared with most usual gases with which it is liable to be mixed.

For example, the published application EP0291462 describes this principle of detecting a gas in air on the basis of thermal conductivity variation. More precisely, this document discloses a gas microsensor employing this principle. The sensitive element of this microsensor consists of a layer of tin oxide, obtained by conventional techniques of chemical attack or deposition by sputtering from a silicon substrate.

It has been envisaged to use a sensor of this type in order to detect hydrogen leaks in the ambient air, which may occur during operation or during shutdown of a fuel cell. With such a sensor, specifically, it is possible to use a microcontroller making it possible to generate an analogue signal representative of the hydrogen concentration measured, and thus to give a warning in the event of a large and unexpected increase in this concentration. However, a safety defect has been observed with such a device, since the signal corresponding to a zero concentration measurement due to effective absence of hydrogen in the air is similar to the signal corresponding to a zero concentration measurement due to a malfunction of the sensor and/or of another element of the device.

Consequently, the existing devices do not offer sufficient reliability since a hydrogen leak may occur without being detected. The object of the present invention is to provide a device making it possible to satisfy this reliability requirement.

SUMMARY OF THE INVENTION

Thus, the present invention relates to a fuel cell system provided with a means for detecting a gas leak, as well as means that make it possible to verify correct operation of the detection device in real time.

More precisely, the present invention relates to a fuel cell system having a stack of electrochemical cells, each of which comprises at least one electrode plate having one face in electrical contact with an electrolyte; at least one tube connected to the said face of each of the cells in a circuit for exchanging a gas with the exterior of the stack;

a detector sensitive to the concentration of hydrogen in the air surrounding the stack; the said sensor comprising a sensitive unit exposed directly to the in situ concentration of a component of the said gas, and at least one microcontroller.

The said fuel cell system is characterized in that the microcontroller comprises means for generating and transmitting analogue concentration information on the basis of the concentration measurement, and means for generating and transmitting an analogue signal of correct operation of the detector.

Advantageously, the gas whose concentration is measured is hydrogen.

Furthermore, in an advantageous embodiment, the microcontroller comprises means for verifying the integrity of one or more components of the monitoring instrument and/or of the sensor. Thus, the presence of this analogue signal of correct operation of the condition monitoring instrument makes it possible to warn the user of a malfunction of an element of the detection device.

Furthermore, in another embodiment of the invention, the microcontroller comprises means for verifying consistency of the concentration measurement with the analogue concentration information generated.

In another embodiment of the invention, the analogue signal of correct operation is a normally high signal. Thus, a high signal is emitted when the device is operating correctly, and a low or zero signal is emitted when a malfunction of the device is detected. This furthermore makes it possible for a supply failure of the device also to be interpreted as a malfunction, since in this case the analogue signal would not be emitted, which corresponds to a zero signal.

In one specific configuration of the invention, the detector or the condition monitoring instrument comprises a single analogue output. In this case, the signal representative of the gas concentration measured and the signal of correct operation must be emitted on a single output. In this configuration, consequently, it is useful for the analogue signal of correct operation to be a normally high signal emitted at regular intervals. This makes it possible to emit two separate items of information on the same output, without these two items of information being confused.

BRIEF DESCRIPTION OF THE FIGURES

Other characteristics and advantages of the invention will emerge from the description given below with reference to the appended drawings, which show embodiments of the subject matter of the invention by way of nonlimiting examples.

DESCRIPTION OF ONE OR MORE EXEMPLARY EMBODIMENTS

Figure 1:
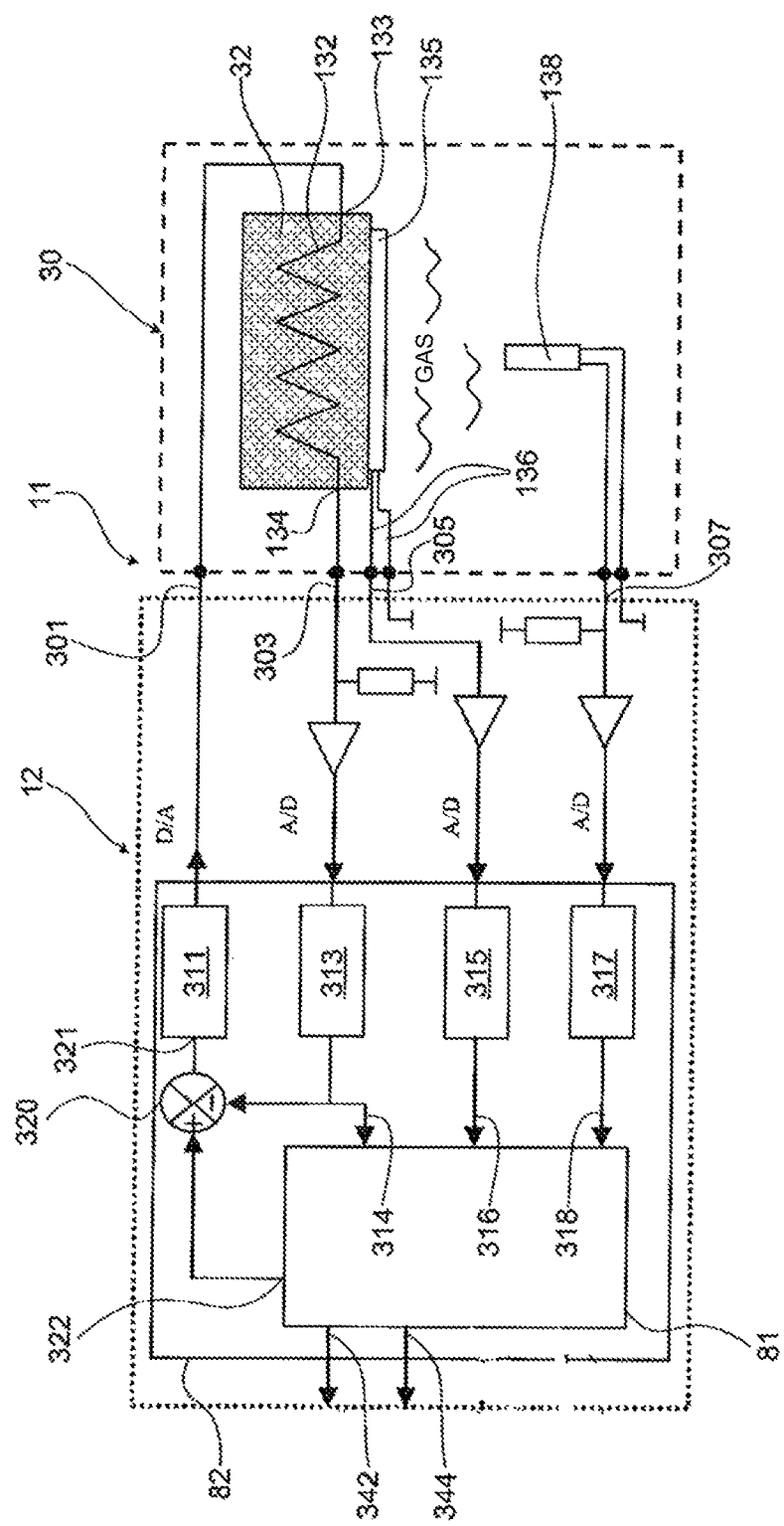
FIG. 1 is a highly simplified diagram of the embodiment of a detector of hydrogen concentration in a gas mixture with its processing electronics, in particular used in a fuel cell, according to the invention.

FIG. 1 shows a diagram of a hydrogen sensor 11 which comprises a panel 32 of sensitive circuits, which is composed of a substrate in the form of a board or a film, for example of silicon. The substrate is coated with an integrated or deposited electrical heating resistor 132, supplied from supply terminals 133 and 134 by a current source controlled by the processing unit 12. One of the faces of the panel 32 comprises a temperature sensor 135, for example formed by a so-called PT100 thermoresistive layer, connected by a set of conductors 136 to the processing unit 12 in order to provide the signals corresponding to the instantaneous temperature of the sensitive unit panel 32, under the double action of heating and heat dissipation into the ambient gas. Furthermore, the hydrogen concentration sensor 11 incorporates a temperature probe 138, for example a PT100 probe, so as to ascertain the temperature of the ambient gas. The physical part of such sensors is described, for example, in patent documents EP 0291 462 B1 of 11 May 1988 and EP 0 501 089 A1 of 25 Feb. 1991.

The processing unit 12 of the hydrogen concentration sensor 11 comprises a digital module 82 connected by four signal lines to the sensitive unit 32. The digital module 82 schematised in FIG. 1 is a synoptic representation of the functions of an algorithm which is installed in a microcontroller and comprises a module 81 for calculating the output quantities of the hydrogen concentration sensor 11, which are intended for the control unit of the fuel cell.

The first line 301 at the output of the processing unit 12 controls, via a digital/analogue converter, the voltage applied to the heating resistor 132 of the sensor of the panel 32. The value of the voltage is controlled on the basis of a stage 311 for regulating the heating power in the control unit 80. In what follows, it will be assumed that the heating resistor is supplied in power regulation mode, although other supply modes of the heating resistor 132 are possible, for example voltage regulation or current regulation.

The second line 303 receives the voltage signal which is the image of the current flowing through the heating resistor 132. This information is converted by an analogue/digital converter A/D at the input of the processing unit 12 in order to be processed by a circuit 313 for monitoring the heating power actually dissipated in the resistor 132 of the hydrogen concentration sensor 11. It can be seen in the diagram that this information, which is sent to a comparator 320 in the digital module 82, is compared with a setpoint value produced at the output 322 of the calculation module 81. In the digital module 82, the product of the comparison of these two quantities controls the input 321 of the heating power regulator 311. The heating of the panel 32 of the sensitive unit 30 is therefore generated by a digital feedback loop on the basis of the heating power setpoint displayed at each instant at the output 322 of the digital module 82. In the case of a constant-voltage supply, the power regulator is replaced with a voltage regulator. Even in the case of voltage regulation, it is important for the power actually dissipated in the heating resistor to be measured by the digital module 82 in order to ensure good precision of the calculation of the hydrogen concentration.

The third line 305 makes it possible to send the analogue output signal of the temperature sensor 135 of the panel 32 to an input of the processing unit 12. After analogue/digital conversion, this signal is processed by a temperature calculator 315 in the digital module 82, which in turn supplies the calculation module 81 with this information.

Lastly, the fourth line 307 corresponds to an input of the processing unit 12 which receives the output voltage of the temperature probe 138 (ambient temperature) and, after analogue/digital conversion, transmits the information to a temperature calculator 317 in the digital module in order to display it at the input of the calculation module 81.

The calculation module 81, which therefore receives information relating to the effective heating power of the sensor, the temperature of the panel 32 and the ambient temperature of the temperature probe 138 on its inputs 314, 316 and 318, makes it possible to determine: the hydrogen concentration and the temperature. The humidity, for its part, may be deduced from other measurements or measured using a specific humidity sensor (not represented).

The sensor comprises an analogue output 342 on which the hydrogen concentration represented by a signal of between 0 and 5 volts is recovered, and a CAN (Controller Area Network) output 344 on which the hydrogen concentration is recovered, furthermore with the humidity and the temperature.

A sensor according to the invention furthermore comprises, in the module 82, means for emitting an autotest signal making it possible to verify correct operation of the sensor in real time. These autotest means thus comprise means for listing all the possible malfunctions of the sensor. Furthermore, the device also comprises instrumentation specific to all the detection elements, making it possible to test the functionalities in real time.

When the autotest means determine that all the functionalities of the sensor are active, a signal of a correct operating state is emitted from the analogue output 342, that is to say on the same output as the signal representing the hydrogen concentration. The malfunction of a single functionality leads to the emission of a "not ok" signal. Preferably, the signal of correct operation is a high signal. Also preferably, the signal of correct operation corresponds to artefacts which are emitted regularly on the output 342, and which therefore make it possible to indicate correct operation of the sensor but without interfering with the transmission of important information, namely the hydrogen concentration.

The choice of a normally high signal results from the wish be able to detect an energy failure in the detector as well. Specifically, an energy failure would lead to an absence of signal, which would thus be interpreted as a malfunction.

Figure 2:
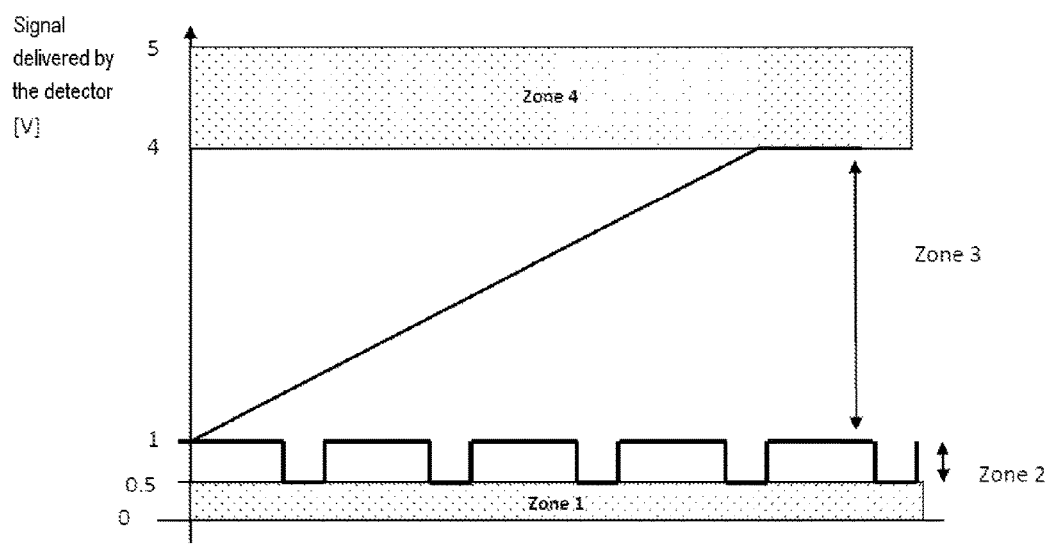
FIG. 2 shows the variation in an analogue signal delivered by a sensor according to the invention.

FIG. 2 thus shows an example of an analogue signal emitted on the output 342 of the detector. It can be seen that the signal is delivered over a range of from 0 to 5 volts.

The autotest signal is a periodic squarewave signal with a base value equal, for example, to 0.5 volts and a high value equal to 1 volt.

The hydrogen detection signal is a proportional signal. Thus, a hydrogen leak is represented on the analogue output by a proportional signal between 1 and 4 volts. The value 1 volt corresponds to a concentration of 0% hydrogen in the air, and the value 4 volts corresponds to a concentration of 4%.

Thus, when the signal delivered by the detector lies between 0 and 0.5 volts, this indicates abnormal behaviour of the detector (zone 1 in FIG. 2).

When the signal delivered lies between 0.5 volts and 1 volt (zone 2 in FIG. 2), this means that the detector is operating normally and no hydrogen leak is detected.

When the signal delivered lies between 1 and 4 volts (zone 3 in FIG. 2), this means that a hydrogen leak is detected.

When the signal delivered lies between 4 and 5 volts, this indicates abnormal behaviour of the detector (zone 4 in FIG. 2).

Thus, an arrangement according to the present invention makes it possible to ensure effective detection of a hydrogen leak and a malfunction of the detector. Specifically, the choice of a periodic autotest signal makes it possible to prevent the case of a signal which remains fixed, for example at a nonzero value. In fact, such a fixed signal could give the impression of normal operation of the detector even though a malfunction might have occurred.

Furthermore, the choice of a nonzero low value of the periodic signal makes it possible to ensure immediate detection of a malfunction of the detector. Specifically, if the autotest signal had a zero base value, this would mean that a zero signal delivered at the output of the sensor would not necessarily be representative of a malfunction of the sensor. It would then be necessary to wait for the signal to change to the high value in order to have confirmation of the state of operation of the detector. However, such a waiting time may prove dangerous in the event of a large hydrogen leak.

A device for detecting a hydrogen leak, making it possible to carry out reliable detection, has therefore been described here. In fact, this detection device makes it possible to distinguish the case of a zero hydrogen measurement because there is actually no hydrogen in the air from the case of a zero concentration measurement because the detector is malfunctioning. This makes it possible to ensure necessary operational safety for the use of an electrochemical reactor, for example in a motorised vehicle.

Furthermore, this detection device is relatively easy to install since the use of a single analogue output for emitting the hydrogen concentration signal and the signal of correct operation makes it possible to limit the number of outputs and therefore the number of wiring operations to be carried out. This also makes it possible to limit the additional costs of such a device.

The invention is not, of course, limited to the examples described and represented, and various modifications may be made thereto without departing from its scope as defined by the appended claims.

The invention claimed is:

1. A fuel cell system, comprising:
a stack of electrochemical cells;
a sensor sensitive to a gas in air surrounding the stack of electrochemical cells, the sensor including a sensitive portion exposed directly to an in situ quantity of a component of the gas, the sensor being structured to output measurement data; and
a microcontroller that performs an algorithm installed therein to generate and output an analog signal corresponding to concentration information, based on the measurement data, and to generate and output an analog signal corresponding to status information of a status of the sensor,
wherein, during operation of the system, the microcontroller causes the analog signal corresponding to the concentration information and the analog signal corresponding to the status information of the status of the sensor to be emitted from a single analog output such that:
during normal operation of the system the analog signal corresponding to the concentration information has a value in a first range or non-zero values,
during normal operation of the system the analog signal corresponding to the status information of the status of the sensor has a value in a second range of non-zero values, indicating a correct operation of the sensor, and
during abnormal operation of the system the analog signal corresponding to the status information of the status of the sensor has a value in a third range of values or in a fourth range of values.

2. The system according to claim 1, wherein the gas is hydrogen.

3. The system according to claim 1, wherein the microcontroller verifies one or both of:
an integrity of the sensor, and
an integrity of one or more components of the microcontroller.

4. The system according to claim 1, wherein the microcontroller verifies a consistency of the measurement data with the analog signal corresponding to the concentration information.

5. The system according to claim 1, wherein the analog signal indicating a correct operation of the sensor is a normally high signal.

6. The system according to claim 5, wherein the normally high signal is emitted at regular intervals.

7. The system according to claim 1, wherein the analog signal indicating a correct operation of the sensor is a periodic signal of a squarewave type.

* * * * *